(12) United States Patent
Sharma (10) Patent No.: US 8,169,299 B2
(45) Date of Patent: May 1, 2012

(54) METHOD AND APPARATUS FOR NEURAL ACTIVITY IDENTIFICATION

(75) Inventor: Jugal Kishore Sharma, Irving, TX (US)

(73) Assignee: OnAsset Intelligence, Inc., Irving, TX (US)

( * ) Notice: Subject to any disclaimer, the term of this patent is extended or adjusted under 35 U.S.C. 154(b) by 1215 days.

(21) Appl. No.: 11/457,108

(22) Filed: Jul. 12, 2006

(65) Prior Publication Data

US 2008/0015801 A1 Jan. 17, 2008

(51) Int. Cl.
*H04Q 1/00* (2006.01)
(52) U.S. Cl. ..................................... 340/5.82
(58) Field of Classification Search .......... 340/5.82, 340/5.52; 600/395; 713/186
See application file for complete search history.

(56) References Cited

U.S. PATENT DOCUMENTS

| | | | | |
|---|---|---|---|---|
| 3,826,243 A * | 7/1974 | Anderson | ..................... | 600/545 |
| 5,470,081 A * | 11/1995 | Sato et al. | ....................... | 463/36 |
| 6,254,536 B1 * | 7/2001 | DeVito | ......................... | 600/300 |
| 7,146,211 B2 * | 12/2006 | Frei et al. | ............................ | 607/2 |
| 7,751,877 B2 * | 7/2010 | Flaherty et al. | ............... | 600/544 |
| 7,885,700 B2 * | 2/2011 | Clark et al. | .................... | 600/372 |
| 2003/0133596 A1 * | 7/2003 | Brooks | .......................... | 382/115 |
| 2004/0058343 A1 | 3/2004 | Macdonald | | |
| 2006/0049946 A1 | 3/2006 | Sullivan et al. | | |

* cited by examiner

*Primary Examiner* — Vernal Brown
(74) *Attorney, Agent, or Firm* — Bruce C. Lutz; Jack D. Stone, Jr.

(57) ABSTRACT

A method and apparatus is provided for creating and recognizing a USN (Unique Signature Number) from an analysis of living entity's (e.g. person, animal or other multi-cellular being having neural activity) emitted electrical or electromagnetic signal in a given, normalized or calm state. This USN may then be used at a later date, in a comparison function of a number of stored USN's, in ascertaining the identity of an entity recently detected as being in proximity to an antenna of the apparatus. A further analysis process can also detect neural activity that is abnormal to that indicated by the USN of a given entity in a calm state and which neural activity may be indicative of excessive aggression, stress or even ill health said given entity.

26 Claims, 5 Drawing Sheets

METHOD AND APPARATUS FOR NEURAL ACTIVITY IDENTIFICATION

FIELD OF THE INVENTION

The present invention relates generally to identifying (ID) individual human and/or other living entities through an analysis of their neural activity in the form of brain waves and/or other electric and electromagnetic field signals generated by that entity.

DESCRIPTION OF THE RELATED ART

A coined term "HFID" is used hereinafter to refer to "Human (and including other living entities having neural activity) Frequency IDentification". Although, it is well known to biometrically identify humans by their fingerprints, a scanning of their retina, their DNA and even by their facial feature or the shape of their ears, applicant is not aware of any prior art that is directed to identifying a human or other living entity as a function of an analysis of the amplitude and frequency components of signals generated by the brain and/or other body portions of that entity.

It is known that neural activity in the brain, of any living entity, sends electrical signals to the rest of the body to perform the various functions of life including the beating of the heart and the movement of limbs and other body parts. Also, it is known that the blood in living entities contains mineral particles such as iron and the flow of blood throughout the body creates a magnetic field. This magnetic field creates a magnetic signal that comprises frequency components similar in nature to the frequency components of the electrical signal generated by neural activity. While this magnetic signal is weak as compared to the strength of the neural activity induced electrical signal, it still comprises a part of the total electromagnetic signal emitted by any living entity. However, the magnetic component of the emitted signal can typically be ignored in situations where the biometric signal detection apparatus is not in direct contact with an entity whose emitted signals are being analyzed.

The electrical portion of a living entity's emitted signal is thus a composite set of signals originating from the brain, the electrical pathways in the body between the brain and body components and the body components such as the heart and muscles. It is known that this composite set of signals can change with health, stress and changes in aggressive behavior.

As is known, finger print ID can be foiled by wearing gloves. DNA ID is a time consuming and expensive process. ID by scanning of the retina, while apparently quite accurate, is very obvious to the entity being scanned.

At the present time, there is no apparatus known to the applicant that can quickly and unobtrusively detect changes in an entity's neural activity in a stressful or aggressive state as compared to the neural activity when that entity is in a normal or calm state. In other words, there is no known apparatus that would raise an alarm when a scanned entity is in an overly stressful and/or potentially very aggressive state of mind.

A need thus exists for ID equipment that can accurately, unobtrusively and quickly ascertain the identity of individuals as well as of livestock and other living entities. There is a further need for apparatus that can unobtrusively detect neural activity that is abnormal for that entity as compared to stored database information relating to that entity.

BRIEF DESCRIPTION OF THE DRAWINGS

For a more complete understanding of one or more embodiments of the present invention and the advantages thereof, reference is now made to the following descriptions taken in conjunction with the accompanying drawings, in which.

DETAILED DESCRIPTION

In the following discussion, numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail. Additionally, for the most part, details concerning network communications, electromagnetic signaling techniques, and the like, have been omitted inasmuch as such details are not considered necessary to obtain a complete understanding of the present invention, and are considered to be within the understanding of persons of ordinary skill in the relevant art.

It is further noted that, unless indicated otherwise, all functions described herein may be performed or implemented in either hardware or software, or some combinations thereof. In a preferred embodiment, however, the functions are performed by a processor such as a computer, microcontroller or an electronic data processor in accordance with code such as computer program code, software, and/or integrated or other electronic circuits that are coded to perform such functions, unless indicated otherwise.

The term USN (Unique Signature Number) will be used herein as an acronym to designate the derived data or resultant set of symbols that is obtained by the present invention when analyzing the raw data frequency spectrum generated by a given individual or other living entity. While a preferred implementation of the invention uses numerals as a basis for the USN, any combination of letters, symbols and/or numbers may be used to create the USN. In a preferred embodiment, the USN will comprise a set of symbols representative of the derived data sampled parameters or characteristics as will be explained in more detail in connection with FIG. 4. It may, in some instances be desirable to additionally, or otherwise, have a set of symbols that merely represent the derived data for purposes of more quickly making a comparison to stored USNs.

As will be realized, the neural activity or brain waves of a living entity change depending upon the activity in which an individual or other entity is engaged. This neural activity, in the form of brain waves, operates in conjunction with the striated muscles, including the heart, and other components of the body to generate the total signal emitted by an entity This total signal emitted is a composite electric/magnetic or biometric signal that is primarily electric. The brainwaves, and thus the total bodily emitted electromagnetic signals, will be somewhat different while sleeping as opposed to sitting, walking or in strenuous and/or stressful work or other activity. Further, it has been determined that the base frequency for individuals tested to date can be as low as 30 Hz and as high as 3000 Hz. However, with a sufficient number of sampling points of the emitted signal frequency spectrum, as detected by the present invention, any entity can be uniquely identified.

The terms "neural activity", "emitted signals", or "biometric signals" as used in this document includes any electrical and/or electromagnetic signals generated by the body as a result of an entity's brain functions or other bodily activity. This signal may be detected indirectly, such as by the use of an antenna, or directly by contact of some portion of the body, including direct contact with the brain cells, with a conductive element. These signals may also be obtained from a plurality of entities in proximity to an appropriate antenna wherein the plurality of entities provides a composite set of signal frequencies over a period of time.

It should be noted here that the entity emitted signals being discussed herein are only indirectly related to EEG (Electroencephalogram) signals which are typically in the 8 to 12 Hz frequency range and are the signals that induce the entity emitted signals that are detected and resolved into a base signal and harmonics thereof as part of the present invention.

Figure 1:
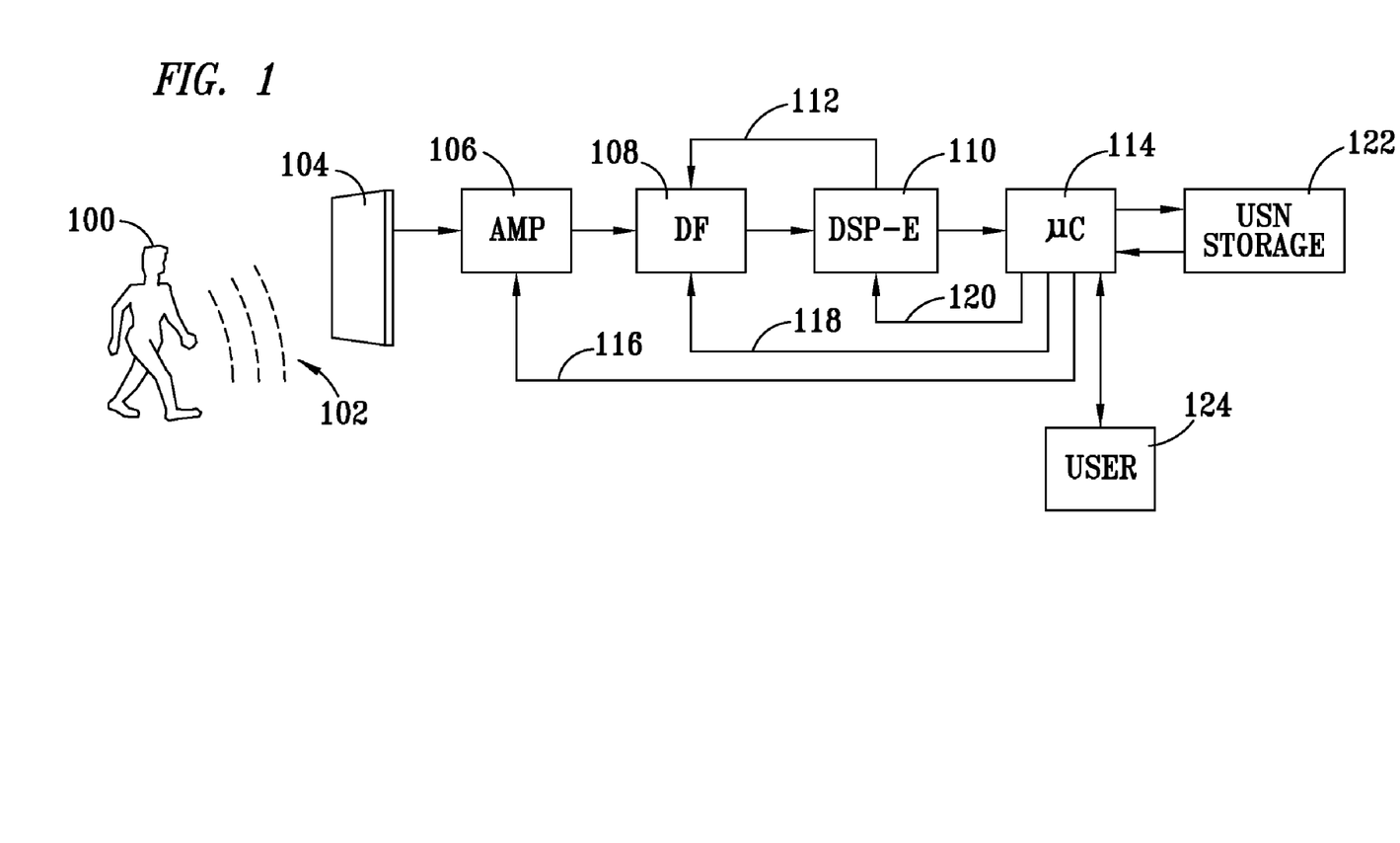
FIG. 1 is a block diagram of the basic components of an entity frequency ID apparatus embodying the features of the invention.

In FIG. 1 a human, or other living entity, generally designated as 100 emits a biometric, primarily electrical, signal shown as dash lines 102. This signal 102 is received by an antenna 104 and passed to an output amplitude adjustable amplifier 106. It may be noted that, in some circumstances, antenna 104 may be any piece of metal including something as innocuous and inconspicuous as a doorknob. In other words, the antenna 104 need not have properties and/or shapes normally associated with receiving radio frequency signals from other electronic equipment. An from amplifier 106 is passed to a digital filter 108 whose output is supplied to a digital signal processing engine 110. An adaptive window feedback signal from engine 110 is supplied on a lead 112 to filter 108 to adjust the bandwidth of the signal being passed toward a value which is likely to eliminate most noise signals while still passing all frequencies that need to be used in determining the USN. This filter, in some instances, may provide not only high and low pass frequency rejection but may additionally provide band frequency rejection intermediate to the high and low pass frequencies. An output of engine 110 is supplied to a processor or microcontroller 114. Processor 114 supplies a feedback signal on a lead 116 to control the amplitude of the signal being output by amplifier 106. Processor 114 also supplies an adaptive algorithm feedback signal on a lead 118 to digital filter 108 to adjust the center frequency of the filter 108 toward the base frequency of the entity whose USN is being determined. Such an adaptive algorithm may be of the type used in conjunction with adaptive filters as shown in a book entitled Digital Processing Handbook (hereinafter "DPH") published by CRC Press LLC in the year 1999 and edited by Vijay K. Madisetti and Douglas B. Williams incorporated in it's entirety herein by reference. Chapter 13 of this book discusses how signals that mainly constitute noise may be detected and filtered out. Chapter 18 and following chapters discuss adaptive filters in detail as well as the algorithms used in the filtering process. Processor 114 further supplies an adaptive algorithm feedback signal on a lead 120 to engine 110 for selecting the harmonics appropriate to a determination of the USN.

As is known in the art, harmonics comprise even and odd multiples of a base frequency. Subharmonics, in a similar manner are even and odd sub-multiples of a base frequency. The selection process, for selecting harmonics to be sampled, will typically pick a given number of harmonics that meet a predetermined set of parameters. As an example, parameters may be those first occurring (lowest frequency) odd harmonics, of an entity's base frequency, that exceed a given minimal detection level and a like number of even harmonics that exceed that level. In such a situation, the number of odd or even harmonics will normally be substantially ½ the total number of samples determined to be necessary to achieve a given level of accuracy for a given number of entities to be searched in a database. Additionally, when subharmonics are detected that meet predetermined parameters such as those that exceed a given minimal level, each of the subharmonics will additionally be used in determining an entity's USN. An approach to obtaining the sampled harmonic points for recording may be found in DPH in chapter 35 commencing on page 759.

Processor 114 is interconnected with a USN storage device 122. The processor 114 is also interconnected to a user or operator shown as a block 124. Processor 114 further preferably includes a computer readable medium (not specifically shown), for storing data and any computer programs to be executed such as may be used in performing the sampling. Block 124 may include a network, such as the internet, and thus the operator of the system may be remote from the antenna 104. Block 124, in some applications, will preferably comprise one or more of monitor, printer, CPU, keyboard and so forth. The storage device 122 may also be remote from the signal detection and comparison hardware.

In many instances, an entity's signal and USN is preferably entered into the system storage 122 with that entity's consent and identifying data such as a name, SSN (social security number) or the like identifying data attached to or associated with the USN. Then in future readings of that entity, the user 124 may substantially instantly identify the individual and, in the case of a business establishment, permit entry of the individual into, or even out of, a given building, secure area and so forth.

In a similar manner, while still in the context of a business establishment, if an individual, whose USN was not in the set of USN's given permission to roam a part of the business premises, passed a given checkpoint, a program within block 114 or 124 can be utilized to raise an alarm condition.

In a different application, such as for monitoring the movement of animals past one or more given points in a field, enclosure or even in a national park, the first detection of a given entity is merely entered in the storage area 122 with some associated identifier such as the date and time and the given point. Each additional time that the entity is detected passing that given point, a count for that entity and given point is incremented. The system may also have other monitoring units for tracking the movement of that entity throughout the field, enclosure or park past each of a plurality of monitored points and a record kept of each occurrence of passage.

As previously briefly stated, the signal emitted by a living entity is a complex and composite electromagnetic signal. This signal is primarily composed of electrical signals from the brain and striated muscles including the heart. However it also has signal components from the electrical pathways in the body and the other body components such as the muscles. As is known, the magnitude of the magnetic component of the emitted signal rapidly diminishes, relative the magnitude of the electrical component of the emitted signal, as a function of the distance of a detection antenna from an entity's body.

Figure 2:
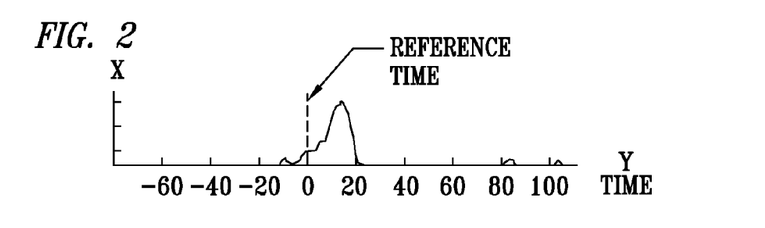
FIG. 2 exemplifies a waveform representation of a signal generated by one specific individual as detected by the apparatus of the present invention over a period of time during which an entity is passing by a signal detecting antenna.

As previously indicated, FIG. 2 comprises an amplitude level or signal strength versus time that might represent one individual's or other entity's base signal with respect to a reference sampling time "0". In other words, the signal received by antenna 104 changes as a given entity approaches and eventually leaves the area in which the equipment can detect the entity's signal.

Figure 3:
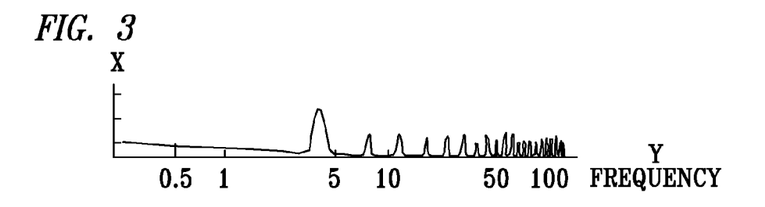
FIG. 3 exemplifies a waveform representation of the base frequency of the signal of FIG. 2 and the harmonics of that base frequency.

When the signal of FIG. 2 is passed through a frequency analyzer, the output of the frequency analyzer may be represented by the graph of FIG. 3 where the signal strength of the base signal and many harmonics are represented.

Figure 4:
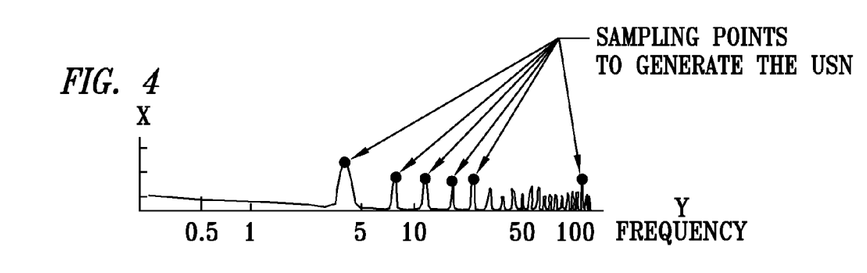
FIG. 4 is representative of how a USN (Unique Signature Number) for the entity represented by the waveform of FIG. 3 might be ascertained.

As illustrated in FIG. 4, a sufficient number of sampling points needs to be taken to be assured of a given probability of accuracy for the intended use. Where the equipment only needs to distinguish the ID of a few hundred humans or animals, only a few points need to be recorded for the USN. Such a situation may well be representative of the 6 sampling points illustrated in FIG. 4. If the system is required to have a high accuracy of distinguishing between the USN's of a large number of entities, the number of points compared in a USN may have to be much larger.

Figure 5:
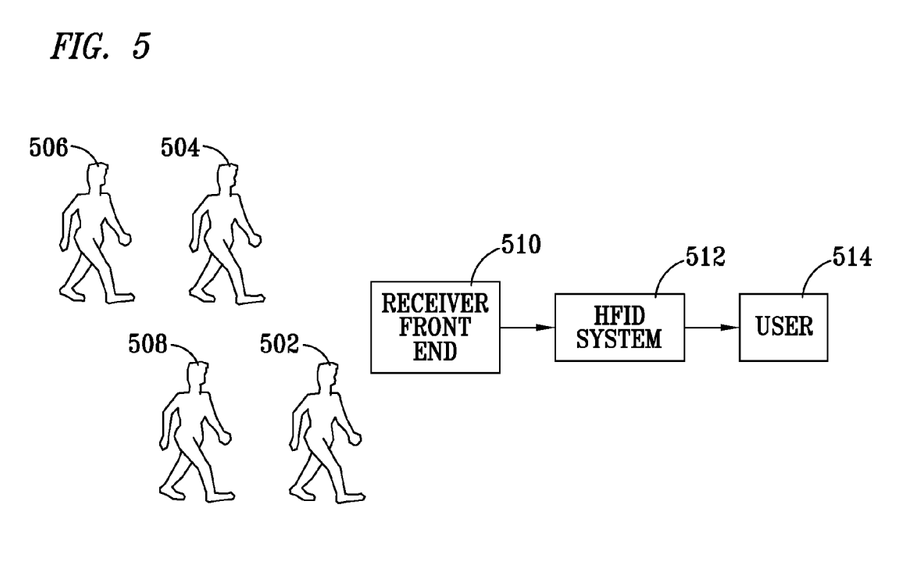
FIG. 5 exemplifies a situation wherein a plurality of living entities emitting signals are substantially simultaneously detected by the system apparatus embodying the features of the invention.

FIG. 5 exemplifies a situation where at least four entities 502, 504, 506 and 508 are passing near enough to an antenna of a HFID receiver front end block 510 whereby the four entitys' emitted signals are detected by the block 510. The signals are supplied to the system 512 for analysis and recording and/or comparison to stored USN's in the system database. The operation is monitored and/or controlled by a user or other operator shown as a block 514. In this figure the block 510 preferably comprises a matrix antenna as discussed infra but accomplishes the same function as antenna 104 of FIG. 1. Likewise, the block 512 operates functionally in substantially the same manner as the blocks 108, 110, 114 and 122 of FIG. 1. As shown, the entities 502 and 508 have substantially passed the primary antenna maximum signal reception point while entities 504 and 506 are approaching the maximum signal reception point of the apparatus antenna. As also illustrated, the entities 502 and 504 are physically closer to the apparatus antenna than are entities 506 and 508. Thus, the maximum amplitude of the signal presented is less for entities 506 and 508 than for the entities 502 and 504.

Figure 6:
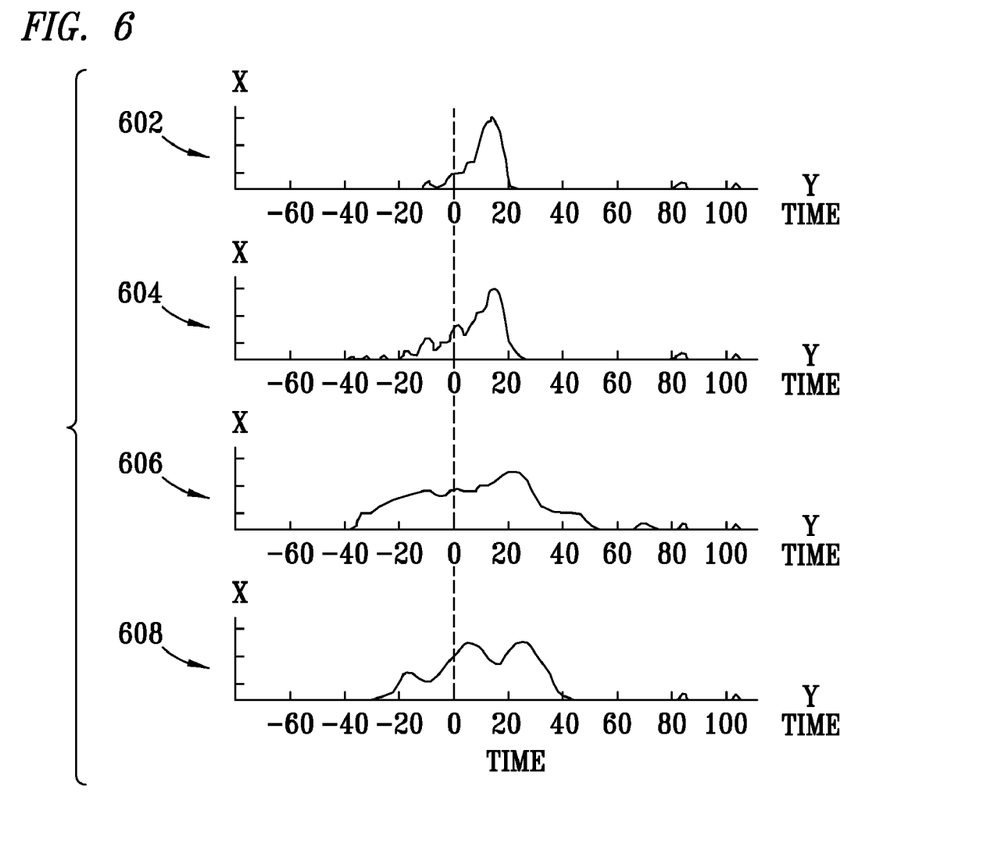
FIG. 6 comprises a set of waveforms representative of the signals generated by four different individuals passing the detection apparatus as a group as shown in FIG. 5.

Four detected signal emissions 602, 604, 606 and 608 are exemplified in FIG. 6 corresponding to the entities 502, 504, 506 and 508 of FIG. 5. The amplitude of these signals are shown for frequencies positive and negative of a system reference time labeled as "0".

Figure 7:
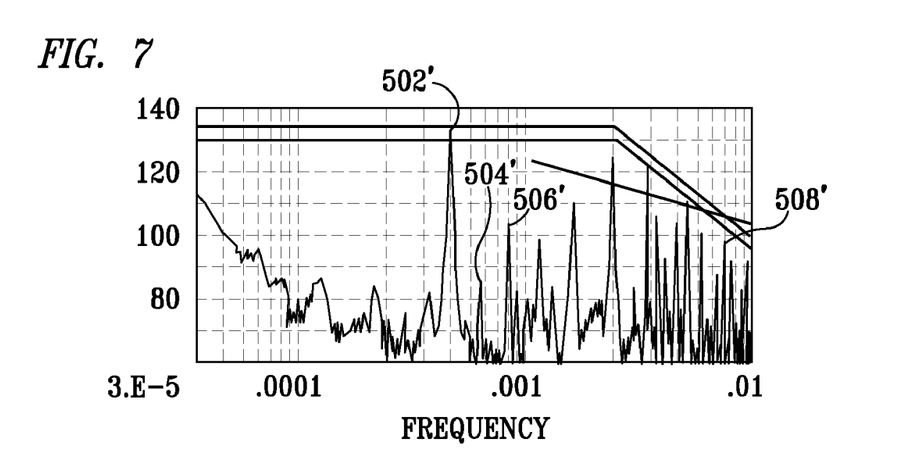
FIG. 7 is representative of the type of composite signal that might be received by an HFID antenna from a plurality of signal emitting entities in addition to the four individuals in the group set forth in the waveforms of FIG. 6.
Figure 8:
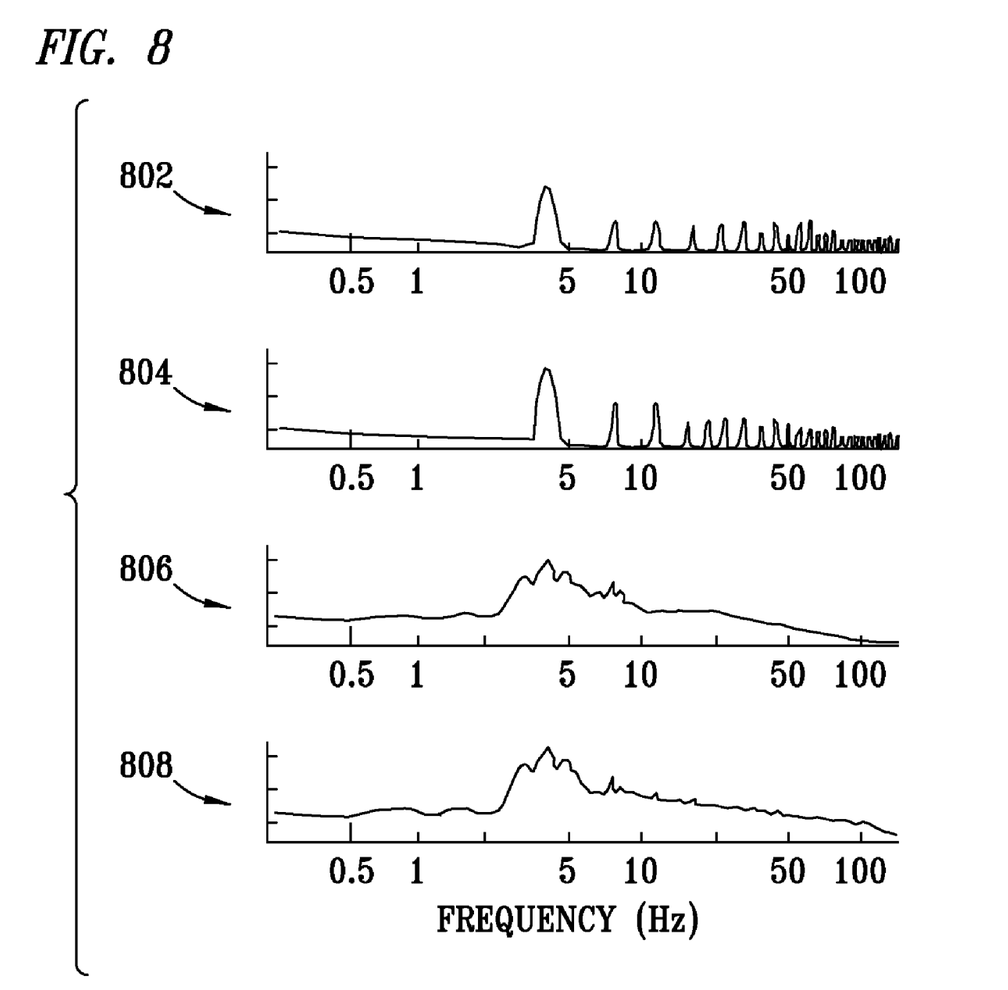
FIG. 8 comprises a set of waveforms representative of the base frequencies of the emitted and detected signals of FIG. 6 and the harmonics of those base frequencies for just the four individuals of the group.

It may be assumed that the system of FIG. 5 is also picking up noise as well as emitted signals from other entities in the area. A composite graph of received signals in the frequency domain is shown in FIG. 7 with the four entities of FIG. 5 shown and labeled as signal amplitude spikes 502', 504', 506' and 508'. The unlabeled spikes in FIG. 7 may be noise or may be other entities in the background not shown in FIG. 5. An analysis of this composite set of signals using conventional DSP procedures can accomplish the separation or resolution and retrieval of the signals generated by each detected entity, in proximity of an appropriate antenna, into a base frequency and a plurality of harmonics (and subharmonics where they exist) as illustrated in FIGS. 6 and 8. If a database of the frequency characteristics of each of the plurality of entities passing the antenna has been established, the identity of each of the plurality of entities can be immediately provided to a user of the HFID detection equipment.

As will be apparent to those skilled in the art, the waveform of FIG. 7 is a complex mixture of signals from different entities, such as people, and this waveform further includes background noise. Thus in order to retrieve resolvable living entity signals, each of the pulses shown must be considered as a fundamental or base frequency. Then an examination of the rest of the received signal frequencies is performed for a predetermined band of frequencies to ascertain what harmonics of that base frequency are detectable. If a sufficient number of harmonics, each exceeding a predetermined amplitude, the set of signals, such as shown in waveform 802 in FIG. 8, is presumed to be a living entity and is temporarily stored as derived data. This procedure is repeated for each and every pulse in the predetermined band of frequencies.

When more than one entity is in the signal pickup range of the antenna, multiple or matrixed antennas are preferred because the extraction of the derived data, as explained above, is more difficult to accomplish with a single antenna than with multiple or matrixed antennas. This is because signals from some entities tend to mask signals of some of the other entities. When using multiple antenna elements in a matrix, a set of spatially distributed signals is obtained for a given group of entities. Appropriate digital signal processing, well-known in the art, in conjunction with the co-relation of the spatially distributed signal enhances the resolution of derived signals for each of a plurality of entities passing an antenna (matrix) at any given time.

The signals of FIG. 6, as separated into base and harmonic frequency components to be used in assigning USN's are shown as 802, 804, 806 and 808 in FIG. 8. When the entity being detected is physically far from the detection apparatus, the noise in the background may prevent an accurate analysis of the components of an entity's emitted signal. Such is the case with entities 506 and 508 which are physically farther from an antenna portion of block 510 than are entities 502 and 504. Thus, as will be noted, the base frequency and corresponding harmonics are not clearly illustrated in waveforms 806 and 808 even though their composite signals 506 and 508 are detectable.

Figure 9A:
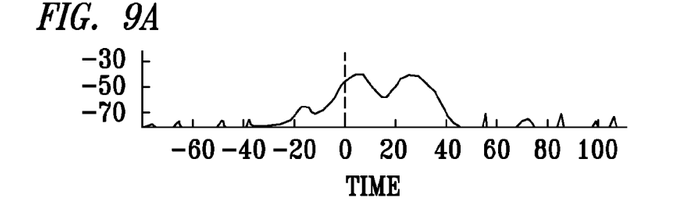
FIGS. 9A through 9F comprise a set of waveforms representing a given entity and illustrating the changes that typically occur in an emitted signal when that entity is under a high level of stress or is in a rundown, sickly or ill state
Figure 9B:
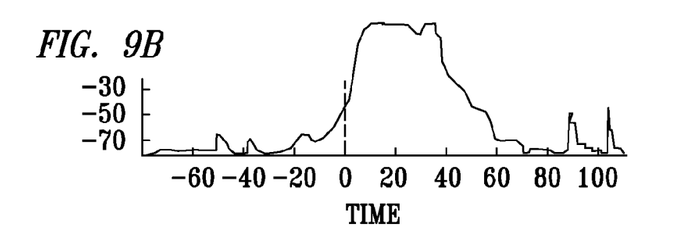
Figure 9C:
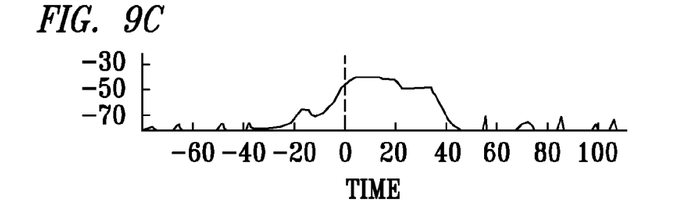
Figure 9D:
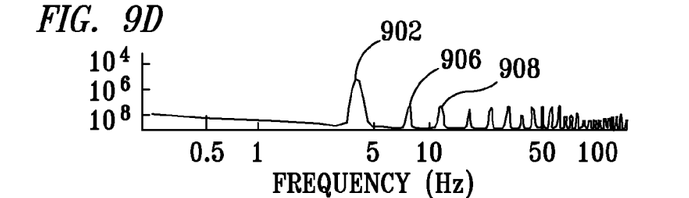
Figure 9E:
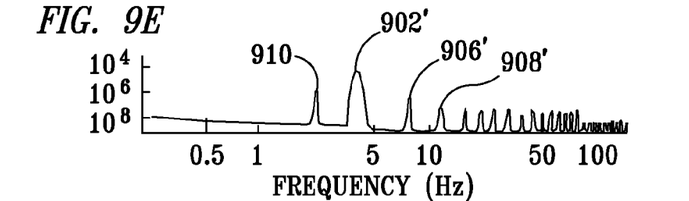
Figure 9F:
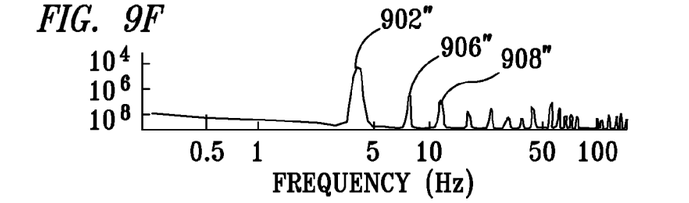

In FIG. 9A a composite emitted signal is presented of an entity in a "calm" or "normal" condition. FIG. 9D illustrates a separated or resolved base signal 902 as well as a plurality of harmonics two of which are designated by reference numbers 906 and 908 of that base signal As mentioned supra, when an entity is in a high stress situation or alternatively when an entity is in an aggressive state, the emitted signal is typically stronger and/or otherwise distinguishable for a baseline value. FIG. 9B illustrates how the emitted signal of the same entity as shown in FIG. 9A may change under a high stress situation. When the signal of FIG. 9B is resolved, as shown in FIG. 9E, it may be observed that while the base frequency 902' has not noticeably changed in amplitude, the first harmonic 906' has increased in amplitude as compared to harmonic 906 in FIG. 9B. Not all harmonics will increase in amplitude as may be observed by comparing the illustrated amplitude of 908' with 908. Although not explicitly shown, the amplitude of other harmonics may increase or decrease in accordance with that entity's neural configuration and associated body components. It may also be noted that for this entity, the amplitude of a subharmonic 910 appears in sufficient magnitude to be detectable when this entity is in a stressed condition. Finally, as also mentioned supra, the amplitude of the emitted signal of an entity is typically less when the entity is sickly or otherwise in ill health. Such a situation is presented in the graphs of FIG. 9C and 9F. The ill health emitted signal of 9C is lower in overall amplitude than the normal emitted signal of FIG. 9A. Likewise, in general, the harmonics resolved, as shown in FIG. 9F, are lower in amplitude even though a few, such 906″ and 908″ are greater in amplitude.

It should be stressed that each entity's resolved set of harmonic signals will be different when in a state other than the "normal" recorded in a database. The discernable difference in the harmonic signals is typically the amplitude of one or more of the harmonic frequencies. The amplitudes of the harmonic frequencies that are different will normally be higher for stress and lower for poor health than for a calm or normal state. However, some of the harmonic frequency signal amplitudes, in some entities, may be less in a stressed state than in a normal state and visa versa for a sickly state versus a normal state. Thus an alarm can easily be generated when an entity is detected whose sampled USN does not substantially match any previously stored USN within a predetermined set of variances because that entity is in an abnormal mental state. The emitted signal of many of these entities will have no subharmonics and a few may have several subharmonics.

A preferred embodiment of the invention uses, as a sampled characteristic, the amplitude of the base frequency signal and the amplitude of a plurality of the harmonics and/or subharmonics for use in deriving a set of symbols to be used as a USN. However, other characteristics may advantageously be used. Thus, one may choose to use total harmonic signal strength for one or more of the sampled values. Likewise, it may be desirable to use pulse slope and so forth for one or more frequencies.

It is understood that the present invention can take many forms and embodiments. Accordingly, several variations may be made in the foregoing without departing from the spirit or the scope of the invention. The carrier signal modulation domains illustrated may have widely varying data rates. Thus, the modulation or demodulation schema is preferably selected for the most appropriate combination of cost, reliability, performance required and the like. As will be apparent from the above, the system, after identifying an individual by comparing a just detected USN with one from a stored USN database or determining that no such USN can be found, may output a signal to operate further equipment. Such equipment may comprise an alarm, an unlock mechanism, a counter or any other operation or procedure based upon the identification, or lack of identification, of a given individual or entity. That is if no USN positive comparison is obtained with a stored set of USNs, a first type electronic operation such as an alarm only may, as an example, be activated. If, on the other hand, a positive USN comparison is obtained with a stored set of USNs, a second type electronic operation may be activated that is a function of the USN identified. If the individual USN identified does not have clearance to proceed an alarm may still be activated. If the individual USN identified does have clearance to proceed a door unlocking mechanism may be activated. Further, additional equipment, such as for example specific designated computers in a room, may be activated that only certain entities, such as the presently USN identified individual, are allowed or permitted to operate.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered desirable by those skilled in the art based upon a review of the foregoing description of preferred embodiments. Accordingly, it is appropriate that the appended claims be construed broadly and in a manner consistent with the scope of the invention.

The invention claimed is:

1. A method of identifying a living entity comprising:
   detecting a naturally occurring, internally generated and emitted signal of an individual;
   resolving the detected naturally occurring, internally generated and emitted signal of an individual into a base and harmonic frequency spectrum comprising a base frequency thereof and a plurality of harmonics of the base frequency; and
   sampling enough points in the base frequency and harmonic frequency spectrum as resolved for formulating a USN (Unique Signature Number) for a living entity.

2. The method of claim 1 wherein:
   storing said USN in a database along with a reference commonly used to identify that individual; and
   comparing a detected USN with stored USN's to ascertain the individual's identity.

3. Apparatus for processing naturally occurring electromagnetic signals generated within and emitted from a living entity:
   antenna means operable to receive naturally occurring living entity generated signals emitted from at least one entity into space that is in proximity to said antenna means; and
   signal processing means, connected to said antenna means for receiving said living entity emitted signals collected by said antenna means, said signal processing means being operable to separate the naturally occurring living entity-emitted signal into at least one base signal component and a one or more base signal harmonic components.

4. The apparatus of claim 3 wherein said signal processing means further comprises:
   sampling means, for deriving a USN (Unique Signature Number) based upon the frequency and characteristic of said base signal component and a plurality of said harmonic components.

5. Apparatus for processing living entity generated naturally occurring emitted signals comprising:
   resolving means operable to resolve the naturally occurring living entity generated and emitted signal of a living entity into a base frequency signal and a plurality of the base frequency signal harmonics; and
   recording means operable to record, in association with said living entity, the frequency and amplitude of said base frequency signal and at least some of said plurality of harmonics.

6. The apparatus of claim 5,
   wherein said recording means is operable to store the recorded frequency and amplitude as numeric values in the form of a USN (Unique Signature Number) along with further identity information pertaining to that entity; and said apparatus further comprising
   comparison means operable to compare a plurality of previously stored USNs with a presently resolved emitted signal whereby the identity of a the entity presently resolved may be ascertained.

7. The apparatus of claim 5 wherein the living entity whose signal is being resolved is a human being.

8. A method of uniquely identifying a living entity naturally occurring emitted neural activity related electrical signals comprising:
    separating a copy of a naturally occurring an electrical signal emitted by a living entity into its separate frequency components;
    sampling a characteristic of each of a plurality of said separate frequency components; and
    recording, in association with said living entity, the characteristic and frequency values of each sampled frequency component.

9. The method of claim 8 comprising the additional step of storing the recorded values as a USN (Unique Signature Number) along with a reference to the specific living entity having that USN in a database with other USNs.

10. A method of uniquely identifying a living entity naturally occurring emitted body generated electrical signals comprising:
    separating a copy of an electrical signal naturally occurring emitted into space adjacent a living entity by a living entity into its separate frequency components;
    sampling a predefined characteristic of each of a plurality of said separate frequency components; and
    assigning at least one descriptor symbol to each sampled value; and
    assembling a plurality of said descriptor symbols into a USN (Unique Signature Number) that uniquely identifies a given living entity.

11. The method of claim 10 wherein:
    the descriptor is a numerical value; and
    the predefined characteristic is amplitude.

12. A method of determining an entity's relative mental health comprising:
    separating a copy of a recently obtained naturally occurring and biometric activity emitted signal of a living entity into its separate frequency components;
    sampling a predefined characteristic of each of a plurality of said separate frequency components;
    comparing the predefined characteristic of at least some of said plurality of separate frequency components with previously recorded derived data; and
    establishing the entity's relative mental health as a result of the magnitude of any differences revealed in the comparing step.

13. A method of uniquely identifying a living entity that generates neural activity related electromagnetic signals comprising:
    separating a copy of an electromagnetic signal naturally occurring and generated by neural activity of a living entity into its separate frequency components;
    sampling a characteristic of each of a plurality of said separate frequency components; and
    recording, in association with said living entity, symbols representative of said sampled frequency components.

14. The method of claim 13 wherein:
    the separate frequency components comprise a base signal and a plurality of harmonics of said base signal; and
    the recorded symbols define a USN (Unique Signature Number) for said living entity.

15. Apparatus for uniquely identifying a living entity that generates neural activity related electromagnetic signals comprising:
    detection means for obtaining and separating a copy of an electromagnetic signal naturally occurring and generated by neural activity of a living entity;
    frequency analysis means, connected to said detection means, for resolving the detected copy into its separate frequency components;
    sampling means, constituting a part of said frequency analysis means, for sampling a predefined characteristic of each of a plurality of said separate frequency components; and
    recording means, interconnected to said frequency analysis means and said sampling means, for recording, in association with said living entity, a unique entity identifier representative of the sampled frequency components.

16. A method of determining an entity's relative mental stress levels comprising:
    separating a copy of a recently obtained naturally occurring and biometric activity generated signal of a living entity into its separate frequency components;
    sampling a characteristic of each of a plurality of said separate frequency components;
    comparing the sampled characteristic of at least some of said plurality of separate frequency components with previously recorded entity identifier values of those frequencies for said living entity; and
    generating an alarm when the compared values deviate by more than predetermined amounts.

17. A computer assisted method of uniquely identifying a living entity that emits biometric activity related electrical signals comprising:
    separating a naturally occurring and entity biometric activity emitted biometric signal into separate frequency components;
    sampling given parameters of each of a plurality of said separate frequency components; and
    assembling a representation of the given parameters into a USN (Unique Signature Number).

18. The method of claim 17 wherein the separate frequency components comprises at least a base frequency and a plurality of harmonics of said base frequency.

19. A method of uniquely identifying a living entity comprising:
    separating an electric signal generated by a living entity into its separate frequency components;
    sampling a characteristic of each of a plurality of said separate frequency components; and
    storing, in association with said living entity, a set of symbols representative of the sampled characteristics.

20. The method of claim 19 wherein the set of symbols defines a USN (Unique Signature Number) derived from a function of the sampled characteristics.

21. Apparatus for processing living entity emitted signals comprising:
    resolving means operable to resolve the naturally occurring and emitted signal of a living entity into a base frequency signal and a plurality of the base frequency signal harmonics; and
    sampling means for sampling a characteristic of each of a plurality of said separate frequency components; and
    storing in association with said living entity a set of symbols representative of the sampled characteristics.

22. The method of claim 1 additionally comprising:
    comparing the just formulated USN with a stored set of USN's; and
    performing a further electronic operation as a function of the result of said comparing.

23. The method of claim 1 additionally comprising:
comparing the just formulated USN with a stored set of USNs to determine whether or not a positive comparison exists;
performing a first type electronic operation if a positive comparison does not exist; and
performing a second type electronic operation when a positive comparison exists.

24. The method of claim 23 wherein the second type electronic operation performed comprises a function of the USN positively compared.

25. Apparatus for identifying a living entity comprising:
emitted signal resolver circuitry operable to separate eletromagnetic signals naturally occurring and emitted by living entities into a base and harmonic frequency spectrum comprising a base frequency thereof and a plurality of harmonics of the base frequency; and
character generator circuitry operable to sample enough points in the base frequency and harmonic frequency spectrum as resolved whereby a USN (Unique Signature Number) for a living entity is generated.

26. Apparatus as claimed in claim 25 additionally comprising:
comparator circuitry operable to compare the just generated USN with a stored set of USNs to determine whether or not a positive comparison exists;
result circuitry operable to perform a first type electronic operation if a positive comparison does not exist and a second type electronic operation when a positive comparison exists.

* * * * *

UNITED STATES PATENT AND TRADEMARK OFFICE
CERTIFICATE OF CORRECTION

PATENT NO. : 8,169,299 B2
APPLICATION NO. : 11/457108
DATED : May 1, 2012
INVENTOR(S) : Jugal Kishore Sharma It is certified that error appears in the above-identified patent and that said Letters Patent is hereby corrected as shown below:

Column 8,
Line 34, after "one" insert -- living --
Line 51, after "occurring" insert -- and --

Column 9,
Line 6, after "occurring" insert -- and --
Line 8, after "occurring" insert -- neural activity --
Line 21, after "occurring" insert -- and --
Line 23, after "occurring" insert -- and --

Signed and Sealed this
Twenty-second Day of January, 2013

David J. Kappos
*Director of the United States Patent and Trademark Office*